United States Patent
Romero-Sarmiento et al.

(10) Patent No.: US 12,292,431 B2
(45) Date of Patent: May 6, 2025

(54) METHOD OF CHARACTERIZING ORGANIC HYDROCARBON COMPOUNDS CONTAINED IN A SOLID DEPOSIT OF A GEOTHERMAL PLANT

(71) Applicant: IFP Energies nouvelles, Rueil-Malmaison (FR)

(72) Inventors: Maria-Fernanda Romero-Sarmiento, Rueil-Malmaison (FR); Herman Ravelojaona, Rueil-Malmaison (FR)

(73) Assignee: IFP ENERGIES NOUVELLES, Rueil-Malmaison (FR)

( * ) Notice: Subject to any disclaimer, the term of this patent is extended or adjusted under 35 U.S.C. 154(b) by 444 days.

(21) Appl. No.: 17/762,764

(22) PCT Filed: Sep. 10, 2020

(86) PCT No.: PCT/EP2020/075403
§ 371 (c)(1),
(2) Date: Mar. 23, 2022

(87) PCT Pub. No.: WO2021/058299
PCT Pub. Date: Apr. 1, 2021

(65) Prior Publication Data
US 2022/0412945 A1    Dec. 29, 2022

(30) Foreign Application Priority Data
Sep. 27, 2019   (FR) ...................... 1910696

(51) Int. Cl.
*G01N 33/24*   (2006.01)
*G01N 5/04*    (2006.01)

(52) U.S. Cl.
CPC ............. *G01N 33/241* (2013.01); *G01N 5/04* (2013.01)

(58) Field of Classification Search
CPC ........ G01N 33/241; G01N 33/26; G01N 5/04; G01N 31/12; Y02E 10/10
See application file for complete search history.

(56) References Cited

U.S. PATENT DOCUMENTS 5,656,814 A * 8/1997 Lurie ...................... G01T 1/115
                                                         250/484.3
10,088,465 B2 * 10/2018 Pillot ................... G01N 33/241
(Continued)

FOREIGN PATENT DOCUMENTS

| FR | 2972803 A1 * | 9/2012 | ........... G01N 33/241 |
| FR | 3021749 A1 | 12/2015 | |
| FR | 3072173 A1 | 4/2019 | |

OTHER PUBLICATIONS

Behar et al. "Rock-Eval 6 Technology: Performances and Developments", Oil & Gas Science and Technology—Rev. IFP, vol. 56, No. 2, Mar.-Apr. 2001, Published Online Dec. 1, 2006, Accessed Online <https://ogst.ifpenergiesnouvelles.fr/articles/ogst/abs/2001/02/behar_v56n2/behar_v56n2.html> (Year: 2001).*

(Continued)

*Primary Examiner* — Jonathan M Dunlap
(74) *Attorney, Agent, or Firm* — Fitch, Even, Tabin & Flannery LLP

(57) ABSTRACT

The present invention relates to a method of characterizing organic hydrocarbon compounds contained in a solid deposit of a geothermal plant, by measuring a quantity of organic hydrocarbon compounds released by a solid deposit sample during heating by pyrolysis according to a temperature sequence such that: from a temperature (T1) ranging between 50° C. and 120° C., the temperature of a rock sample is raised to a temperature (T2) ranging between 180° C. and 220° C. This temperature (T2) is then maintained for a predetermined duration. The temperature of the sample is raised to a temperature (T3) ranging between 330° C. and (Continued)

370° C. This temperature (T3) is maintained for a predetermined duration. The temperature of the sample is thereafter raised to a temperature (T4) ranging between 630° C. and 670° C.

13 Claims, 1 Drawing Sheet

(56) References Cited

U.S. PATENT DOCUMENTS

| | | | | |
|---|---|---|---|---|
| 10,302,617 | B2* | 5/2019 | Pillot | G01N 33/241 |
| 2015/0346179 | A1* | 12/2015 | Pillot | G01V 9/005 |
| | | | | 702/2 |
| 2018/0106776 | A1* | 4/2018 | Pillot | G01N 33/241 |

OTHER PUBLICATIONS

Romero-Sarmiento et al. "New Rock-Eval Method for Characterization of Unconventional Shale Resource Systems", Oil & Gas Science and Technology—Rev. IFP Energies nouvelles (2016) 71, 37 <https://ogst.ifpenergiesnouvelles.fr/articles/ogst/pdf/2016/03/ogst140208.pdf> (Year: 2016).*

Romero-Sarmiento et al. "Artificial thermal maturation of source rocks at different thermal maturity levels: Application to the Triassic Montney and Doig formations in the Western Canada Sedimentary Basin", Organic Geochemistry 97 (2016) 148-162, <https://doi.org/10.1016/j.orggeochem.2016.05.002> (Year: 2016).*

Romero-Sarmiento et al. "Corrosion inhibitors and lubricants characterization using the Rock-Eval® Shale Play™ method: Case studies to determine the origin of geothermal scales", Geothermics 101 (2022) 102357, <https://doi.org/10.1016/j.geothermics.2022.102357> (Year: 2022).*

Haas-Nüesch Ruth et al., "Mineralogical characterization of scalings formed in geothermal sites in the Upper Rhine Graben before and after the application of sulfate inhibitors," Geothermics, vol. 71, Jan. 2018, pp. 264-273, XP085287969, ISSN: 0375-6505, DOI: 10.1016/J.GEOTHERMICS.2017.10.006.

Peralta, G. L., et al., "Physicochemical characteristics and leachability of scale and sludge from Bulalo geothermal system, Philippines," Geothermics, vol. 25, issue 1, Feb. 1996, pp. 17-35, https://doi.org/10.1016/0375-6505(95)00033-X.

International Search Report PCT/EP2020/075403, mailed Dec. 10, 2020.

* cited by examiner

[Fig 1]
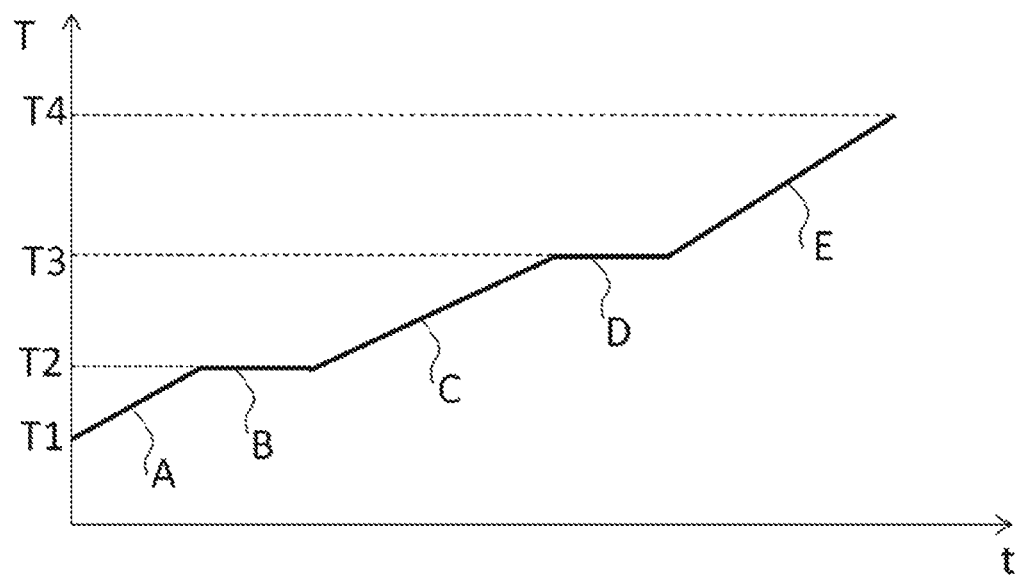
[Fig 2]
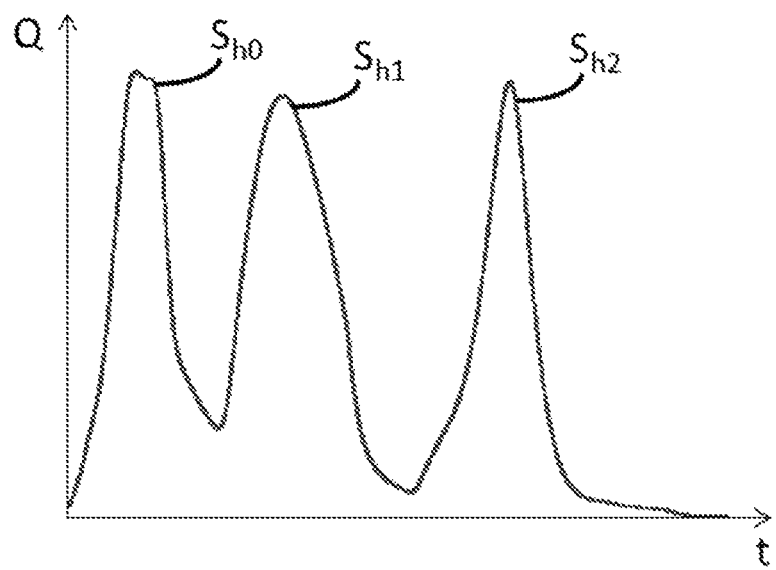

METHOD OF CHARACTERIZING ORGANIC HYDROCARBON COMPOUNDS CONTAINED IN A SOLID DEPOSIT OF A GEOTHERMAL PLANT

CROSS-REFERENCE TO RELATED APPLICATIONS

This application is a U.S. national phase application filed under 35 U.S.C. § 371 of International Application No. PCT/EP2020/075403, filed Sep. 10, 2020, designating the United States, which claims priority from French Patent Application No. 1910696, filed Sep. 27, 2019, which are hereby incorporated herein by reference in their entirety.

FIELD OF THE INVENTION

The present invention relates to the field of geothermal energy, more specifically to the field of monitoring and characterizing geothermal plant fouling.

Diversification of the different energy sources allows to reduce fossil fuel dependence and thus to meet the challenges of energy transition. In this context, the global market for geothermal power generation is expected to double in the next ten years.

The geothermal resource exploits the natural geothermal gradient (temperature increase with depth) of the Earth, which may be very variable depending on the sites. Thus, to capture the geothermal energy, a fluid is circulated in the subsoil, at a greater or lesser depth depending on the desired temperature and according to the local thermal gradient. This fluid may be naturally present in the rock (aquifer) or it may be purposely injected into the subsoil. The fluid heats up upon contact with the subsurface rocks and it flows back to the surface laden with calories, which are transmitted in a heat exchanger. The fluid is thereafter reinjected into the medium, once cooled and filtered.

Geothermal plants for converting thermal energy to electrical energy thus generally comprise a primary circuit (closed-loop water circuit) and a secondary circuit (electricity generation circuit). The secondary circuit can comprise a heat exchanger containing for example a heat-transfer fluid, which is heated and pressurized by means of the calories drawn from the water moving upward from the subsoil. The fluid can then expand at the inlet of a steam turbine, thus enabling conversion of the mechanical energy to electricity via an alternator. The heat-transfer fluid can subsequently be cooled, then recompressed prior to being sent back, in liquid form, to the exchanger.

Proper operation of a geothermal plant therefore involves monitoring the constituent elements of the primary and/or secondary circuits, and notably their fouling. Indeed, these circuits notably comprise many pipes, joints, filters, etc. In particular, the fluid flowing in the primary circuit can be laden with highly aggressive mineral salts and thus generate solid deposits. Moreover, the chemicals used within a geothermal plant may also generate solid deposits on some elements of a plant, thus compromising the operating life of this plant. Various chemicals such as corrosion inhibitors or lubricants, which may themselves generate deposits on the filters of a plant for example, are indeed conventionally used.

Monitoring and characterizing the formation of solid deposits in a geothermal plant is therefore a recurrent technical problem. In particular, it is important to characterize the chemical composition of solid deposits in a geothermal plant, so as to be able to predict their precipitation and to develop strategies for preventing their formation.

Besides, it is also important to determine whether a solid deposit observed on an element of a geothermal plant can originate from chemicals (such as lubricants or corrosion inhibitors) used within the context of the operation of a geothermal plant.

BACKGROUND OF THE INVENTION

The following documents are mentioned in the description:
Haas-Nüesch R., Heberling F., Schild D, Rothe, J., Dardenne K., Jähnichen S., Eiche E., Marquardt C., Metz V., Schäfer T. (2018) Mineralogical characterization of scalings formed in geothermal sites in the Upper Rhine Graben before and after the application of sulfate inhibitors. Geothermics 71:264-273.
Peralta, G. L., Graydon, J. W., Kirk, D. W. (1996). Physicochemical characteristics and leachability of scale and sludge from Bufalo geothermal system, Philippines. Geothermics 25:17-35.

The solid deposits present in geothermal plants are conventionally analysed using various techniques such as: X-ray diffraction (XRD), radioactivity quantification, elemental chemical analysis via ICP-AES (ICP Atomic Emission Spectrometry), ICP-MS (Inductively Coupled Plasma Mass Spectrometry), SEM-EDX (Scanning Electron Microscopy and Energy Dispersive X-ray analysis), XPS (X-ray Photoelectron Spectroscopy), EA-IRMS (Isotope Ratio Mass Spectrometry coupled to an Elemental Analyzer), Raman and XANES (X-ray Absorption Near Edge Spectroscopy) spectroscopy, among others.

Documents (Peralta et al., 1996; Haas-Nüesch et al., 2018), which describe analyses carried out using some of the above techniques, can notably be mentioned.

The present invention is an alternative to the various techniques listed above. The method according to the invention has the advantage of being fast (of the order of ten minutes), quantitative (the ratio of a mass of organic hydrocarbon compounds to the mass of analysed sample is determined), versatile (solid or liquid samples can be analysed). Furthermore, no prior sample preparation is required.

Besides, the invention can allow to rapidly compare the organic phase of solid deposits observed on an element of a geothermal plant with that of chemicals such as corrosion inhibitors and lubricants, in order to investigate whether these chemicals have caused the formation of the solid deposits observed in this geothermal plant.

SUMMARY OF THE INVENTION

The present invention relates to a method of characterizing organic hydrocarbon compounds contained in a solid deposit of a geothermal plant. The method according to the invention comprises at least applying the following steps to a sample of said deposit:
  A) heating at least said sample in an inert atmosphere according to a temperature sequence and continuously measuring at least one representative quantity of said organic hydrocarbon compounds released during at least said temperature sequence, said temperature sequence being such that:
    a) from a first temperature value ranging between 50° C. and 120° C., the temperature of said sample is raised according to a first temperature gradient ranging between 1° C./min and 50° C./min up to a second temperature value ranging between 180° C. and 220° C., and said sample is maintained at said second temperature value for a first predetermined duration, b) from said second temperature value, the temperature of said sample is raised according to a second temperature gradient ranging between 1° C./min and 50° C./min up to a third temperature value ranging between 330° C. and 370° C., and said sample is maintained at said third temperature value for a second predetermined duration, c) from said third temperature value, the temperature of said sample is raised according to a third temperature gradient ranging between 1° C./min and 50° C./min up to a fourth temperature value ranging between 630° C. and 670° C., B) from at least said measurement of said representative quantity of said organic hydrocarbon compounds released by said solid deposit sample during said temperature sequence, characterizing said organic hydrocarbon compounds contained in said solid deposit of said geothermal plant.

According to one implementation of the invention, at the beginning of step a), said sample can be maintained at said first temperature for a duration ranging between 2 and 6 minutes.

According to one implementation of the invention, said first and second durations can range between 2 and 4 minutes.

According to one implementation of the invention, said first temperature value can range between 80° C. and 120° C.

According to one implementation of the invention, said second temperature value can range between 190° C. and 210° C.

According to one implementation of the invention, said third temperature value can range between 340° C. and 360° C.

According to one implementation of the invention, said fourth temperature value can range between 640° C. and 660° C.

According to one implementation of the invention, said organic hydrocarbon compounds contained in said solid deposit of said geothermal plant can be characterized from at least one curve of said measurement of said representative quantity of said organic hydrocarbon compounds released by said solid deposit sample during said temperature sequence.

According to one implementation of the invention, said organic hydrocarbon compounds contained in said solid deposit of said geothermal plant can be characterized by determining at least one area under at least a portion of said measurement curve of the quantity of organic hydrocarbon compounds released by the solid deposit sample.

According to one implementation of the invention, said organic hydrocarbon compounds contained in said solid deposit of said geothermal plant can be characterized by determining at least one representative parameter of said quantity of organic hydrocarbon compounds contained in said sample according to a formula of the type:

$$Q_C = \frac{SurfQ}{m}$$

wherein SurfQ corresponds to at least said area under at least said portion of said measurement curve of the representative quantity of organic hydrocarbon compounds released by the solid deposit sample, and m corresponds to the initial mass of said sample.

According to one implementation of the invention, said organic hydrocarbon compounds contained in said solid deposit of said geothermal plant can be characterized by determining at least one representative parameter of said quantity of organic hydrocarbon compounds contained in said sample according to a formula of the type:

$$Q_C^{Shx} = \frac{SurfShx}{m}$$

with Shx selected from among {Sh0, Sh1, Sh2}, and where SurfSh0, SurfSh1 and SurfSh2 respectively correspond to the area under said measurement curve of said representative quantity of organic hydrocarbon compounds released by said first sample between said first and second temperatures, said second and third temperatures, and said third and fourth temperatures, and m corresponds to the initial mass of said sample.

According to one implementation of the invention, said organic hydrocarbon compounds contained in said sample of said solid deposit of said geothermal plant can be characterized by comparing said measurement curve of said representative quantity of said organic hydrocarbon compounds released by said solid deposit sample during said temperature sequence with at least one reference curve determined for a chemical used in said geothermal plant.

According to one implementation of the invention, said reference curve for said chemical used in said geothermal plant can be determined by applying at least steps a), b) and c) to a sample of said chemical.

According to one implementation of the invention, said comparison can be made by determining at least one quadratic mean of the differences between said measurement curve of said representative quantity of said organic hydrocarbon compounds released by said solid deposit sample during said temperature sequence and said reference curve determined for said chemical.

According to one implementation of the invention, said comparison can be made by comparing said areas under said measurement curve of said representative quantity of said organic hydrocarbon compounds released by said sample of said solid deposit respectively between said first and second temperatures, and/or said second and third temperatures, and/or said third and fourth temperatures of said temperature sequence with areas under said reference curve determined for said chemical respectively between said first and second temperatures, and/or said second and third temperatures, and/or said third and fourth temperatures of said temperature sequence.

BRIEF DESCRIPTION OF THE FIGURES

Other features and advantages of the invention will be clear from reading the description hereafter of embodiments given by way of non-limitative example, with reference to the accompanying figures wherein:

FIG. 1 shows a variant of the inert-atmosphere temperature sequence of the method according to the invention, and FIG. 2 illustrates a measurement curve of a representative quantity of the organic hydrocarbon compounds released by a solid deposit sample of a geothermal plant during the temperature sequence of FIG. 1.

DETAILED DESCRIPTION OF THE INVENTION

In general terms, the invention relates to a method of characterizing organic hydrocarbon compounds contained in a solid deposit present in a geothermal plant. The solid deposit can for example be present on or in an element of the geothermal plant, such as a filter. The method according to the invention requires at least one sample of the solid deposit present in the geothermal plant, taken for example from an element such as a filter of the plant.

The method according to the invention comprises at least the following steps:
1) Inert-atmosphere temperature sequence
2) Characterization of the organic hydrocarbon compounds.

According to one implementation of the invention, step 1) can be repeated for at least another sample, corresponding to a sample of a chemical used in a geothermal plant, such as a corrosion inhibitor or a lubricant. Step 1) of the method according to the invention is carried out for a solid deposit sample of a geothermal plant, but it can also be applied to a sample of a chemical used in the geothermal plant.

The steps of the method according to the invention are detailed hereafter.

1) Inert-Atmosphere Temperature Sequence

In this step, the solid deposit sample is heated in an inert atmosphere (i.e. a pyrolysis is conducted, or the sample is heated in the absence of oxygen) according to a sequence of predefined time-varying temperatures, and at least one representative quantity of the organic compounds released during at least this temperature sequence is continuously measured.

According to the invention, the inert-atmosphere temperature sequence is defined as follows:
a) from a first temperature value denoted by T1, ranging between 50° C. and 120° C., the temperature of said sample is raised according to a first temperature gradient ranging between 1° C./min and 50° C./min up to a second temperature value denoted by T2, ranging between 180° C. and 220° C., and said sample is maintained at said second temperature value T2 for a first predetermined duration,
b) from said second temperature value T2, the temperature of said sample is raised according to a second temperature gradient ranging between 1° C./min and 50° C./min up to a third temperature value denoted by T3, ranging between 330° C. and 370° C., and said sample is maintained at said third temperature value T3 for a second predetermined duration,
c) from said third temperature value T3, the temperature of said sample is raised according to a third temperature gradient ranging between 1° C./min and 50° C./min up to a fourth temperature value denoted by T4, ranging between 630° C. and 670° C.

This temperature sequence is advantageous because it allows differentiated release of the light, heavy and extra-heavy hydrocarbon compounds contained in a sample. An implementation of this temperature sequence is illustrated in FIG. 1. Thus, this implementation of the temperature sequence of the method according to the invention comprises three successive heating steps (ramps corresponding to segments A, C and E in FIG. 1), separated by two temperature maintenance steps (isothermal stages corresponding to segments B and D in FIG. 1). More precisely, this temperature sequence starts with a low first temperature T1 ranging between 50° C. and 120° C., which allows to measure more completely the quantity of low to high molecular weight hydrocarbon compounds present in a sample. Furthermore, the method according to the invention comprises, between two heating steps (ramps A, C and E in FIG. 1), temperature maintenance steps (isothermal stage B, corresponding to a temperature T2 ranging between 180° C. and 220° C., and isothermal stage D corresponding to a temperature T3 ranging between 330° C. and 370° C. in FIG. 1), which allows to reach with certainty the end of the thermovaporization of the thermovaporizable hydrocarbon compounds in the temperature range considered.

FIG. 2 shows an example of a measurement curve (or program) of the representative quantity of organic hydrocarbon compounds released by a sample during the inert-atmosphere temperature sequence as described in FIG. 1. The presence of three peaks denoted by Sh0, Sh1 and Sh2, representative of the quantity of hydrocarbon compounds released during the various heating steps, can be observed in this figure. More precisely, peak Sh0 corresponds to the hydrocarbon compounds released between first temperature T1 and second temperature T2, i.e. during segments A and B of FIG. 1. This peak Sh0 is representative of the lighter thermovaporizable hydrocarbon compounds. Peak Sh1 corresponds to the hydrocarbon compounds released between second temperature T2 and third temperature T3, i.e. during segments C and D of FIG. 1. This peak Sh1 is representative of the heavy thermovaporizable hydrocarbon compounds. Peak Sh2 corresponds to the hydrocarbon compounds released between third temperature T3 and fourth temperature T4, i.e. during segment E of FIG. 1. This peak Sh2 is representative of the extra-heavy thermovaporizable hydrocarbon compounds.

According to one implementation of the present invention, the sample can be maintained at first temperature T1 for a non-zero duration preferably greater than a half-minute, and more preferably ranging between 2 and 6 minutes. This preliminary step of maintaining the sample at first temperature T1 enables heating up of the sample and/or release of the extra-light hydrocarbon compounds present in a sample.

According to one implementation of the invention, the sample can be maintained at second temperature T2 for a first predetermined non-zero duration preferably greater than a half-minute, and more preferably ranging between 2 and 4 minutes.

According to one implementation of the invention, third temperature T3 can be maintained for a second predetermined non-zero duration preferably greater than a half-minute, and more preferably ranging between 2 and 4 minutes.

According to a preferred embodiment, the first and/or second and/or third temperature gradient can range between 20° C./minute and 30° C./minute.

According to one implementation of the invention, the value of first temperature T1 can range between 80° C. and 120° C.

According to one implementation of the invention, the value of second temperature T2 can range between 190° C. and 210° C.

According to one implementation of the invention, the value of third temperature T3 can range between 340° C. and 360° C.

According to one implementation of the invention, the value of fourth temperature T4 can range between 630° C. and 670° C.

Steps a), b) and c) of the method according to the invention can be carried out using a device comprising at least one oven for performing at least one inert-atmosphere heating according to a predefined temperature sequence, and means for continuous measurement of at least one quantity of organic compounds released by the sample subjected to inert-atmosphere heating. Such a device may correspond to the Rock-Eval® device (IFP Energies nouvelles, France) developed by the applicant and described notably in patent EP-2,342,557 (U.S. Pat. No. 8,796,035). According to one implementation of the invention, the means for continuous measurement of the organic compounds released during pyrolysis can be a flame ionization detector (FID).

2) Characterization of the Organic Hydrocarbon Compounds

This step consists in characterizing the organic hydrocarbon compounds contained in the solid deposit of the geothermal plant using the measurement of the representative quantity of organic compounds released by the solid deposit sample subjected to the inert-atmosphere temperature sequence as described in step 1 above.

According to one embodiment of the invention, the organic hydrocarbon compounds contained in the solid deposit of the geothermal plant can be characterized from the measurement curve of the representative quantity of organic compounds released by the solid deposit sample subjected to the inert-atmosphere temperature sequence.

According to one implementation of the invention, the organic hydrocarbon compounds contained in the solid deposit of the geothermal plant can be characterized at least by determining the area (or surface area) of at least a portion of the measurement curve of the representative quantity of organic compounds released by the solid deposit sample subjected to the inert-atmosphere temperature sequence.

According to one implementation of the invention, the organic hydrocarbon compounds contained in the solid deposit of the geothermal plant can be characterized by determining the areas (or surface areas) of at least one of the three peaks Sh0, Sh1 and Sh2 described above and corresponding to the hydrocarbon compounds released during steps a), b) and c) of the inert-atmosphere temperature sequence according to the invention respectively. In other words, according to this implementation of the invention, the organic hydrocarbon compounds present in the solid deposit sample taken from the geothermal plant are characterized by determining at least one of the parameters denoted by SurfSh0, SurfSh1, SurfSh2, respectively corresponding to the area under peaks Sh0, Sh1 and Sh2 of the measurement curve of the hydrocarbon compounds released during the pyrolysis temperature sequence applied to the sample, given in mV (millivolt).

According to one implementation of the invention, the organic compounds contained in the solid deposit can be characterized by determining a parameter, denoted by $Q_c$ hereafter, representative of the quantity of organic compounds contained in the solid deposit sample by means of a formula of the type:

$$Q_C = \frac{SurfQ}{m}$$

wherein SurfQ corresponds to at least a portion of the area under the measurement curve of the representative quantity of organic compounds released by the solid deposit sample, and m corresponds to the initial mass (i.e. before pyrolysis) of the solid deposit sample. According to one implementation of the invention, SurfQ can for example correspond to the area under the measurement curve of the representative quantity of organic compounds released by the solid deposit sample between two predetermined temperatures of the inert-atmosphere temperature sequence, for example in order to more specifically target organic compounds with a molecular weight of interest to the specialist.

According to an implementation of the invention, one can determine:

a parameter $Q_c^{sh0}$ representative of the quantity of light (whose number of carbon atoms is less than about 20) thermovaporizable organic compounds contained in the solid deposit sample by means of a formula of the type:

$$Q_C^{Sh0} = \frac{SurfSh0}{m},$$

and/or a parameter $Q_c^{sh1}$ representative of the quantity of heavy (whose number of carbon atoms substantially ranges between 20 and 30) thermovaporizable organic compounds contained in the solid deposit sample by means of a formula of the type:

$$Q_C^{Sh1} = \frac{SurfSh1}{m},$$

and/or a parameter $Q_c^{sh2}$ representative of the quantity of extra-heavy (whose number of carbon atoms is greater than about 30) thermovaporizable organic compounds contained in the solid deposit sample by means of a formula of the type:

$$Q_C^{Sh2} = \frac{SurfSh2}{m}$$

wherein SurfSh0, SurfSh1, SurfSh2 respectively correspond to the area under peaks Sh0, Sh1, Sh2 of the measurement curve of the organic hydrocarbon compounds released during the pyrolysis temperature sequence applied to the solid deposit sample, given in mV, and m corresponds to the initial mass (before pyrolysis) of the solid deposit sample, in mg.

According to a main variant of the method of the invention, the organic compounds contained in the solid deposit taken from the geothermal plant are characterized by comparing a measurement curve of the representative quantity of organic compounds released during the inert-atmosphere temperature sequence with at least one reference curve relative to a chemical, such as a lubricant or a corrosion inhibitor, used during the operation and/or the maintenance of the geothermal plant.

According to one implementation of this main variant of the invention, the reference curve relative to a chemical used during the operation of the geothermal plant is obtained by applying step 1 as described above to a sample of said chemical, according to the same temperature sequence as for the solid deposit sample.

According to one implementation of this main variant, the comparison between at least a portion of the measurement curve of the representative quantity of organic compounds released during the inert-atmosphere temperature sequence by the solid deposit sample and the corresponding portion (i.e. between the same temperatures, or after the same pyrolysis duration with the same temperature sequence) of the reference curve relative to a chemical used in the geothermal plant is made by means of at least one measurement of a distance between the two curves. According to an implementation of the invention, measurement of the distance between the two curves can consist in measuring a difference between the two curves, using for example a quadratic mean or rms (root mean square) mean and a predefined threshold on this difference measurement. In other words, if the measurement of this difference between the two curves is below the predefined threshold, it can be concluded that the solid deposit results from the use of said chemical. Otherwise, it can be concluded that this chemical is not the cause of the solid deposit observed in the geothermal plant. According to one implementation of the invention, the threshold can range between 10% and 30%, and it is preferably 20%.

Alternatively or cumulatively, the surface areas of peaks Sh0, Sh1 and Sh2 as described above and determined both for the solid deposit sample and the chemical sample can be compared to conclude whether the chemical is the cause or not of the solid deposit observed in the geothermal plant. For example, if the difference between the surface areas of peaks Sh0 and/or Sh1 and/or Sh2 determined both for the solid deposit and the chemical is below a predefined threshold, it can be concluded that the solid deposit results from the use of said chemical. Otherwise, it can be concluded that this chemical is not the cause of the solid deposit observed in the geothermal plant. According to one implementation of the invention, the threshold can range between 10% and 30%, and it is preferably 20%.

Alternatively or cumulatively, the values of parameters $Q_c$ and/or $Q_c^{sh0}$ and/or $Q_c^{sh1}$, and/or $Q_c^{sh2}$ as described above and determined both for the solid deposit sample and the chemical sample can be compared to conclude whether the chemical is the cause or not of the solid deposit observed in the geothermal plant. For example, if the difference between the values of parameters $Q_c$ and/or $Q_c^{sh0}$ and/or $Q_c^{sh1}$, and/or $Q_c^{sh2}$ determined both for the solid deposit and the chemical is below a predefined threshold, it can be concluded that the solid deposit results from the use of said chemical. Otherwise, it can be concluded that this chemical is not the cause of the solid deposit observed in the geothermal plant. According to one implementation of the invention, the threshold can range between 10% and 30%, and it is preferably 20%.

The invention claimed is:

1. A method of characterizing organic hydrocarbon compounds contained in a solid deposit of a geothermal plant, characterized in that at least the following steps are applied to a sample of the deposit:
   A) heating at least the sample in an inert atmosphere according to a temperature sequence and continuously measuring at least one representative quantity of the organic hydrocarbon compounds released during at least the temperature sequence, the temperature sequence being such that:
      a) from a first temperature value ranging between 50° C. and 120° C., the temperature of the sample is raised according to a first temperature gradient ranging between 1° C./min and 50° C./min up to a second temperature value ranging between 180° C. and 220° C., and the sample is maintained at the second temperature value for a first predetermined time,
      b) from the second temperature value, the temperature of the sample is raised according to a second temperature gradient ranging between 1° C./min and 50° C./min up to a third temperature value ranging between 330° C. and 370° C., and the sample is maintained at the third temperature value for a second predetermined time,
      c) from the third temperature value, the temperature of the sample is raised according to a third temperature gradient ranging between 1° C./min and 50° C./min up to a fourth temperature value ranging between 630° C. and 670° C.,
   B) characterizing the organic hydrocarbon compounds contained in the solid deposit of the geothermal plant from at least one curve of the measurement of the representative quantity of the organic hydrocarbon compounds released by the solid deposit sample during the temperature sequence by comparing the measurement curve of the representative quantity of said organic hydrocarbon compounds released by the solid deposit sample during the temperature sequence with at least one reference curve determined for a chemical used in the geothermal plant.

2. A method as claimed in claim 1 wherein, at the beginning of step a), the sample is maintained at the first temperature T1 for a duration ranging between 2 and 6 minutes.

3. A method as claimed in claim 1, wherein the first and second predetermined times range between 2 and 4 minutes.

4. A method as claimed in claim 1, wherein the first temperature value ranges between 80° C. and 120° C.

5. A method as claimed in claim 1, wherein the second temperature value ranges between 190° C. and 210° C.

6. A method as claimed in claim 1, wherein the third temperature value ranges between 340° C. and 360° C.

7. A method as claimed in claim 1, wherein the fourth temperature value ranges between 640° C. and 660° C.

8. A method as claimed in claim 1, wherein the organic hydrocarbon compounds contained in the solid deposit of the geothermal plant are characterized by determining at least one area under at least a portion of the measurement curve of the quantity of organic hydrocarbon compounds released by the solid deposit sample.

9. A method as claimed in claim 8, wherein the organic hydrocarbon compounds contained in the solid deposit of the geothermal plant are characterized by determining at least one representative parameter of the quantity of organic hydrocarbon compounds contained in the sample according to a formula of the type:

$$Q_C = \frac{SurfQ}{m}$$

wherein SurfQ corresponds to at least the area under at least the portion of the measurement curve of the representative quantity of organic hydrocarbon compounds released by the solid deposit sample, and m corresponds to the initial mass of the sample.

10. A method as claimed in claim 8, wherein the organic hydrocarbon compounds contained in the solid deposit of the geothermal plant are characterized by determining at least one representative parameter of the quantity of organic hydrocarbon compounds contained in the sample according to a formula of the type:

$$Q_C^{Shx} = \frac{SurfShx}{m}$$

with Shx selected from among {Sh0, Sh1, Sh2}, and where SurfSh0, SurfSh1 and SurfSh2 respectively correspond to the area under the measurement curve of the representative quantity of organic hydrocarbon compounds released by the first sample between the first and second temperatures, the second and third temperatures, and the third and fourth temperatures, and m corresponds to the initial mass of the sample.

11. A method as claimed in claim 1, wherein the reference curve for the chemical used in the geothermal plant is determined by applying at least steps a), b) and c) to a sample of the chemical.

12. A method as claimed in claim 1, wherein the comparison is made by determining at least one quadratic mean of the differences between the measurement curve of the representative quantity of the organic hydrocarbon compounds released by the solid deposit sample during the temperature sequence and the reference curve determined for the chemical.

13. A method as claimed in claim 1, wherein the comparison is made by comparing the areas under the measurement curve of the representative quantity of the organic hydrocarbon compounds released by the sample of the solid deposit respectively between the first and second temperatures, and the second and third temperatures, and the third and fourth temperatures of the temperature sequence with areas under the reference curve determined for the chemical respectively between the first and second temperatures, and the second and third temperatures, and the third and fourth temperatures of the temperature sequence.

* * * * *